(12) United States Patent
Kert

(10) Patent No.: US 6,893,258 B1
(45) Date of Patent: May 17, 2005

(54) DENTAL MATERIAL CURING APPARATUS

(75) Inventor: Jimmie Kert, Copenhagen (DK)

(73) Assignee: CMS-Dental Aps, Copenhagen (DK)

( * ) Notice: Subject to any disclaimer, the term of this patent is extended or adjusted under 35 U.S.C. 154(b) by 92 days.

(21) Appl. No.: 10/170,037

(22) Filed: Jun. 11, 2002

(51) Int. Cl.[7] .................................................. A61L 1/00
(52) U.S. Cl. ....................................................... 433/29
(58) Field of Search ............................ 433/29; 362/800, 362/109, 119, 120

(56) References Cited

U.S. PATENT DOCUMENTS

| | | | |
|---|---|---|---|
| 4,112,335 A | 9/1978 | Gonser | 315/241 |
| 4,229,658 A | 10/1980 | Gonser | 250/504 |
| 4,385,344 A | 5/1983 | Gonser | 362/32 |
| 5,147,204 A | 9/1992 | Patten et al. | 433/229 |
| 5,316,473 A * | 5/1994 | Hare | 433/29 |
| 5,487,662 A * | 1/1996 | Kipke et al. | 433/37 |
| 5,885,082 A | 3/1999 | Levy | 433/215 |
| 6,318,996 B1 | 11/2001 | Melikechi et al. | 433/29 |
| 6,331,111 B1 * | 12/2001 | Cao | 433/29 |
| 6,514,075 B1 * | 2/2003 | Jacob | 433/29 |

FOREIGN PATENT DOCUMENTS

| | | | |
|---|---|---|---|
| EP | 1090608 A1 | 4/2001 | A61C/19/00 |
| EP | 1138276 A1 | 10/2001 | A61C/19/00 |
| JP | 2000070292 | 3/2000 | A61C/19/06 |
| WO | WO01/26576 | 4/2001 | A61C/5/00 |

\* cited by examiner

*Primary Examiner*—Cary E. O'Connor
(74) *Attorney, Agent, or Firm*—K. David Crockett, Esq.; Crockett & Crockett

(57) ABSTRACT

A light emitting apparatus for curing a photocurable dental prosthesis in a patient's tooth that comprises a LED carrying part connected to a handle. The LED carrying part comprises a first plurality of LEDs directed to a first side of the tooth, and a second plurality of LEDs directed to a second side of the tooth. The present invention also relates to a method of curing a photocurable dental prosthesis in a patient's tooth, in which a light emitting apparatus is provided that comprises LEDs that are mounted on a substrate, the substrate being covered with a clear coating embedding the LEDs, and the LEDs being placed so proximate to the photocurable dental prostheses that the smallest distance between the outer surface of the clear coating and the outer surface of the photocurable dental prostheses is less than 2 mm. The LED carrying part can be connected to a handle for grasping by a user's hand, or be provided with a structure for engaging an opposite tooth so that it can be held in place between the patient's teeth.

18 Claims, 3 Drawing Sheets

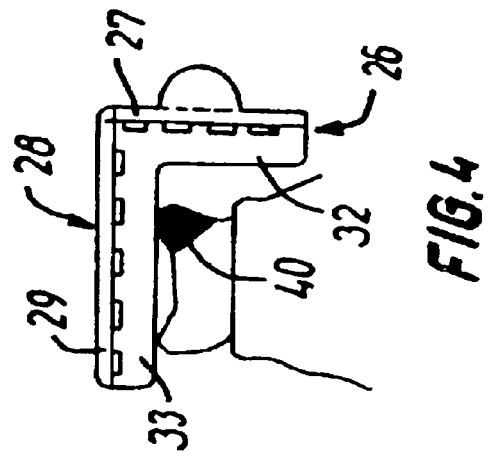
FIG. 4
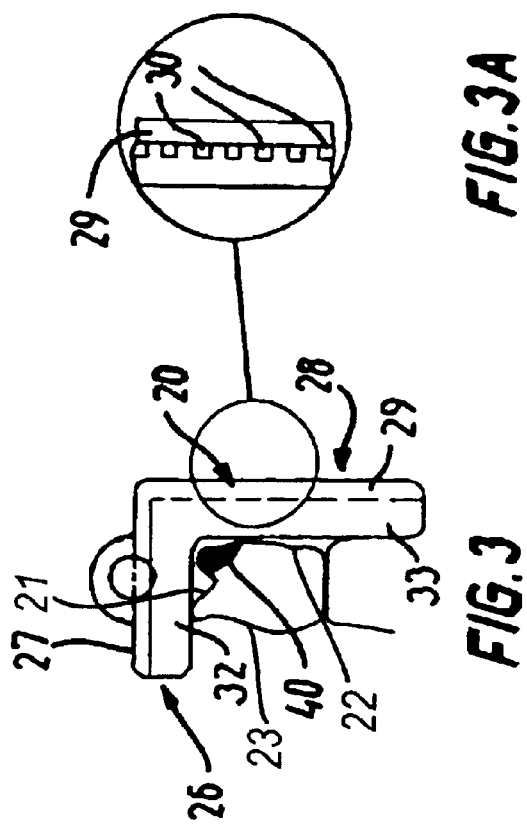
FIG. 3A
FIG. 3
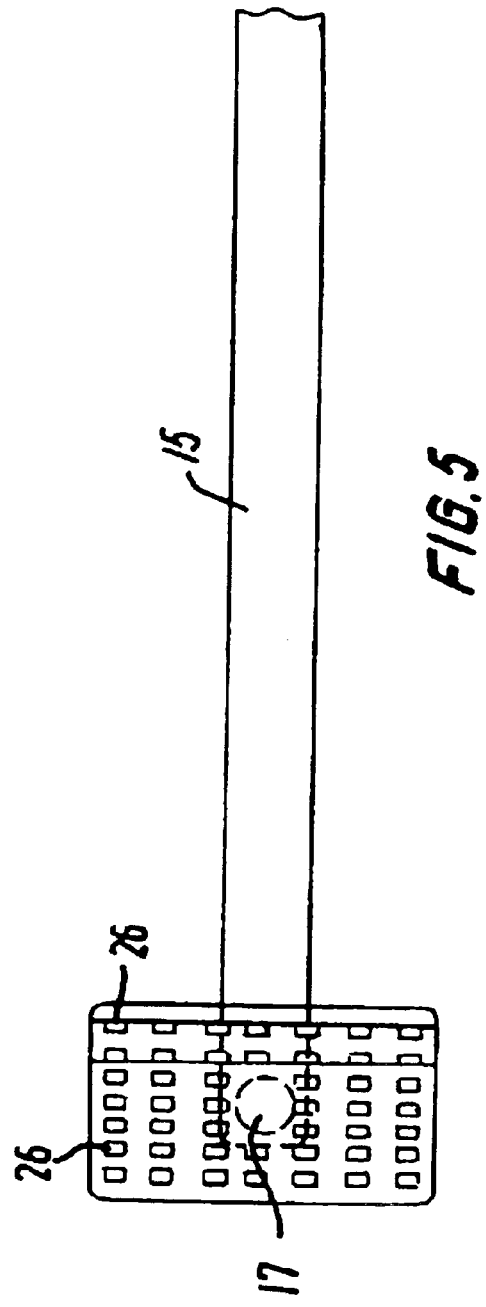
FIG. 5

DENTAL MATERIAL CURING APPARATUS

FIELD OF THE INVENTIONS

The inventions described below relate to a curing apparatus for photocurable dental compositions. In particular, the inventions relate to a curing apparatus for photocurable dental compositions using a light emitting diode (LED) proximate to the composition to be cured. These tools are in particularly used by dentists for curing materials in dental prostheses. Further, the inventions relate to a method of curing photocurable dental prosthesis in a patient's tooth, in which a plurality of LEDs is positioned proximate to the prosthesis.

BACKGROUND ART

Light cured polymeric materials are widely used in the field of dentistry for adhesion, sealing and restoration, and may be cured or hardened upon exposure to a source of radiation. Such photoactive materials are cured generally when exposed to a specific radiation spectrum depending on the type of photoactivator being used, and most commonly, a photo-activated chemical reaction is initiated by the application of a high intensity blue light having a wavelength of 400–500 nanometer.

Photocurable dental materials are a convenience to the dentist as curing processes can be initiated when desired. For example, an amount of photocurable filling material is properly placed in a tooth cavity. A source of light next to the tooth cavity is then positioned proximate to the material and activated to initiate polymerization and subsequent curing of the composition to secure the repair.

The first generation of photocured dental materials were hardened by the application of concentrated beams of ultraviolet (UV) radiation. Apparatuses for producing concentrated beams of UV radiation are known from e.g. U.S. Pat. Nos. 4,112,335 and 4,229,658. Later, visible light curable dental materials were used and dental radiation guns for producing concentrated visible light were provided like that disclosed in U.S. Pat. No. 4,385,344. However, a relatively high divergence of about 25 degrees of the light beam from such visible light sources reduces penetration into the dental prosthesis material, leading to their relative inefficiency and unreliability for photo-curing dental materials that are thicker than about two millimeters.

Photocurable dental materials have also been developed that are hardened by exposure to radiant energy in a preselected spectral range. Typically, a photo-activated chemical reaction in many photo-curable dental materials is initiated by application of a high intensity blue light having a wavelength of 400–500 nanometers. Since the light sources employed typically produce the entire visible light spectrum as well as some non-visible radiation, a reflector is coated to reflect only visible light, and the filters are selected to substantially block non-visible radiation and visible light other than blue light in the range of 400–500 nanometers, in order to produce the desired range of radiation, as shown for example in U.S. Pat. No. 5,147,204.

A disadvantage of the curing apparatuses of the prior art discussed above is that the majority of the light produced by the curing apparatuses is in an ineffective wavelength, and consequently, most of the light supplied to the teeth is simply dissipated as heat. This is not desirable as the pulp in the teeth is very sensitive to heat.

Laser-based radiation sources have also been employed, using for example, a Nd YAG laser producing radiation at a wavelength of about 1060 nanometers, in combination with a frequency doubling material as disclosed for example in U.S. Pat. No. 5,885,082. In the instance that a laser source is used, the beam must be de-focused to cover the area being cured and this is done by varying by hand the distance between the dental composition and the laser dental gun.

More recently, LED light sources have been used to provide a high intensity light nearly exclusively in the effective wavelength, e.g. about 470 nanometers, as shown in for example U.S. Pat. No. 6,318,996, EP-1 090 608, and JP-2000-070292.

A disadvantage with these prior art curing lights is that the LEDs cannot effectively be brought close enough to the material to be cured in order to obtain a sufficient curing depth. Further, the tip of the light guides used is relatively small, so that only an area of about 0.3 cm$^2$ can effectively be exposed to radiation. Thus, it is difficult to treat a larger dental prosthesis evenly.

SUMMARY

The devices and methods described below provide for easy placement of a light source in a dental patient's mouth, so that resinous fillings and restorations (prostheses) can be cured and hardened by the light. A light emitting apparatus is provided in a form which can be placed in close proximity to a photocurable dental prosthesis. The light emitting apparatus includes an array of light sources, preferably light emitting diodes. The LED arrays may be covered with a coating that is transparent to the light emitted by the light sources, and this coating may formed into a lens. The array of light sources may be fixed on an L-shaped or U-shaped frame which is held in place with a shaft which is rotatably secured to the frame. The frame may instead be fixed to a biting surface or biting cup which the patient holds in place by biting on the surface or cup so as to engage the surface or cup with the teeth opposing the tooth which is being repaired.

BRIEF DESCRIPTION OF THE DRAWINGS

In the following detailed portion of the present description, the inventions will be explained in more detail with reference to the exemplary embodiments shown in the drawings, in which FIG. 3 is a detailed view on the LED carrier of the apparatus shown in FIGS. 1 & 2, as applied to a premolar tooth, FIG. 4 is a detailed view on the LED carrier of the apparatus shown in FIGS. 1 & 2, as applied to a molar tooth, FIG. 5 is a top view in detail on the LED carrier part and the connection rod.

DETAILED DESCRIPTION

Figure 1:
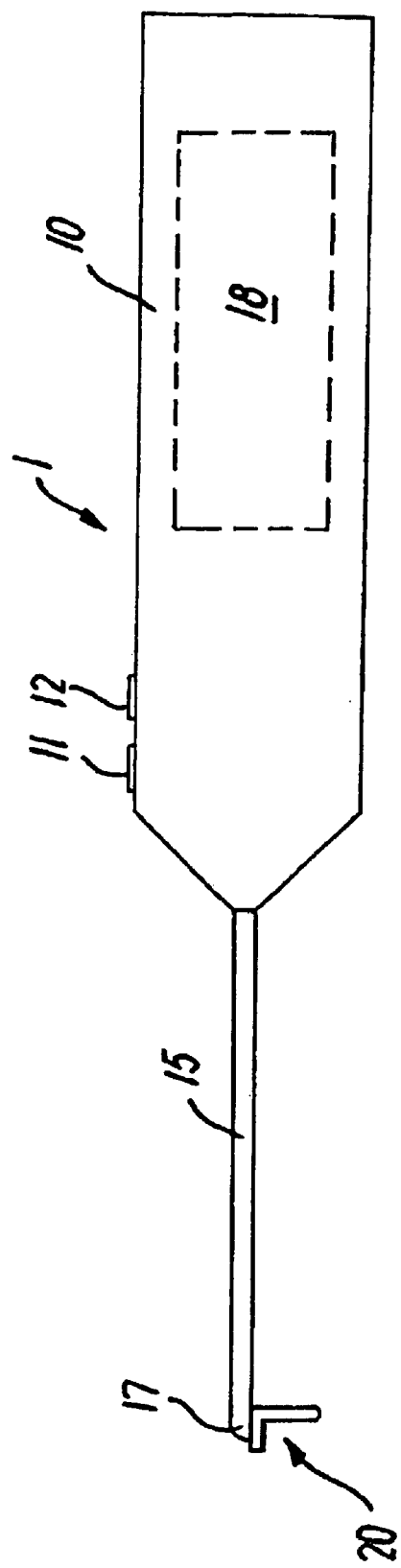
FIG. 1 is a diagrammatic side view of a first preferred embodiment of the curing apparatus.
Figure 2:
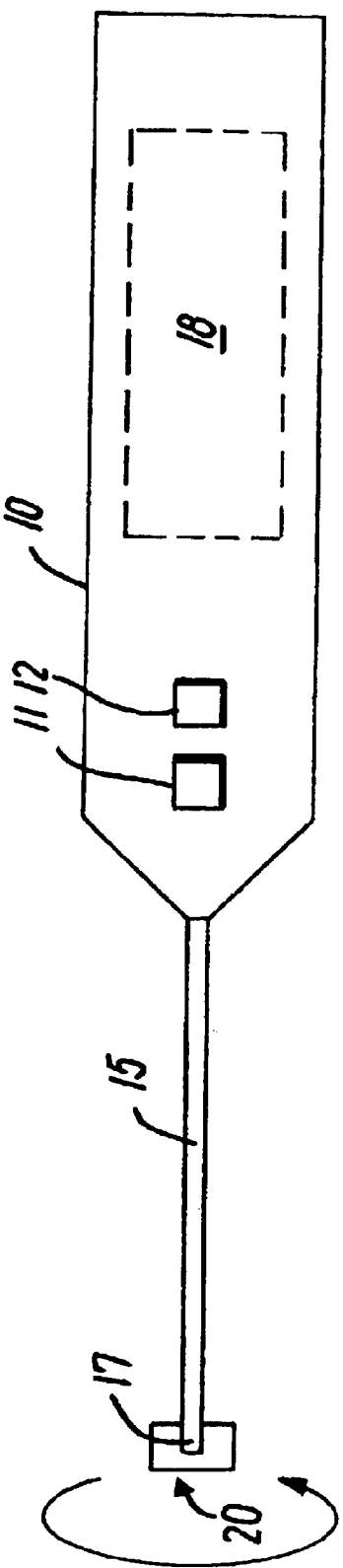
FIG. 2 is a diagrammatic top view on the apparatus shown in FIG. 1.

In the following detailed description, the inventions will be described by the preferred embodiments. In FIGS. 1 & 2, a curing apparatus 1 according to a first preferred embodiment is shown. The curing apparatus 1 comprises an elongated handle 10 shaped for operator convenience in positioning a LED carrier 20 proximate to a dental prosthesis 40. The handle 10 has a basically hollow cylindrical shape and contains a power source 18 with electric circuitry and a battery for powering the LEDs 30 on the LED carrier 20. Suitable power sources for powering a plurality of LEDs are well known in the industry. On/off switches 11,12 are conveniently arranged on the handle 10.

A rod 15 extends from a distal part of the handle 10 to a ball joint 17. The joint may, however, also be of a type with more- or with fewer degrees of freedom such as, i.e. a flexible shaft or a pivot joint (not shown). As best shown in FIG. 5, the ball joint 17 connects the LED carrier 20 to the rod 15. The LED carrier is thus rotatable in three different directions relative to the rod 20 and can be placed in practically any desired angle relative to the rod 20. Wires (not shown) connect the power source 18 to the LEDs 30.

As best shown in FIGS. 3 and 4, the LED carrier 20 comprises two wings 26,28 attached to one another to form a body with a L-shaped cross-section which may be placed close to the tooth so that the surfaces of the wings are apposite the surface of the teeth being treated. In FIG. 3, the first wing 26 is longer than the second wing 28, and the LED carrier is situated in close proximity to a premolar tooth. The first wing 26 is disposed proximate the occlusal surface 21 of the premolar tooth, and the second wing 28 is disposed proximate the lingual surface 22 (or buccal surface 23) of the tooth. Each wing 26,28 is build up of a substrate layer made of printed circuit board 27,29. A plurality of surface mounted type LEDs 30 is mounted to each of the printed circuit boards 27,29. The LEDs 30 are evenly distributed over the circuit boards 27,29 in a regular pattern. Preferably, LEDs with an integral focusing lens are used, it is however also possible to use LEDs without an integral focusing lens. The printed circuit boards 27,29 are covered by a clear coating 32,33 embedding the LEDs 30. Instead of a clear coating, any other form of transparent protection may be used such as a transparent plastic plate. The clear coating is optically transparent to the wavelength of light emitted by the light sources, and need not be "transparent" to the human eye.

Typically, the circuit board 27 has a width of 1 cm and a length of 1 cm. The circuit board 29 has typically a width of 1 cm and a length of 0.5 cm. At the connection between the two circuit boards 27,29 their width is preferably equal. The width and the length of the circuit boards 27,29 is chosen such that they at least cover the extent of the dental prosthesis 40 to be cured, and preferably, at least cover the extent of the complete tooth in which the prosthesis 40 is placed. Variations to the above mentioned size for the circuit boards 27,29 are possible, i.e. for treating dental prostheses of different sizes. Typically, premolar teeth can be treated with a LED carrier 20 with smaller wings 26,28 and large molar teeth may require a LED carrier 20 with larger wings.

The angle between the wings 26,28 is shown to be about 90°, but it may have any angle between 80 to 100°. The wings may perhaps be fixed at more acute or obtuse angles for treating prostheses of uncommon dimensions. The optimum angle depends on the relative position of the dental prosthesis 40 to be cured and on the shape of the tooth containing the prosthesis to be cured.

The printed circuit boards 27,29 are provided with a plurality of surface mounted LEDs 30. The LEDs 30 are evenly distributed over the circuit boards 27,29 so that a uniform radiation intensity is obtained. An example of an LED useful in practicing the present inventions is manufactured by Toyoda Gosei Co. Ltd, part no E1S03-AB1A7-02. These LEDs emit radiation in the range of about 465 to about 470 nanometer with an output of 44 milicandela and are operated with maximum 3,9 volt and 20 miliampere. Fifty LEDs of this type are mounted per $cm^2$ of circuit board. The radiation intensity at the top surface of the clear coating 32,33 is about 135 $mw/cm^2$. Other suitable light sources may be used, such as semiconductor laser diodes or any other miniature light source which can dispersed over the circuit boards and can be safely used within the mouth.

The handle 10 is held by the operator, typically a dentist, and the LED carrier 20 is placed in the oral cavity proximate the tooth containing the prosthesis 40 to be treated. The prosthesis 40 may be a filling, overlay, cap, crown or other restoration material, referred to as a prosthesis, which is designed to be formed within the mouth and cured or hardened after installation. The connection rod 15 will protrude at least partially from the oral cavity and the LED carrier 20 is rotated relative to the rod 15 into a suitable position proximate the dental prosthesis 40 to be cured. The LED carrier 20 is preferably placed such that the smallest distance between the surface of the clear coating 32,33 and the surface of the prosthesis 40 is less than 2 mm. On premolar teeth the LED carrier 20 is usually placed as shown in FIG. 3. On molar teeth the LED carrier 20 is typically placed as shown in FIG. 4. with the long wing 28 opposite the occlusal surface and the short wing 26 disposed in opposing relation to the buccal or lingual surface of the tooth. Often, a dental prosthesis 40 is located on a corner of a tooth. In such a case, the LED carrier 20 can be placed such that the prosthesis 40 is radiated from two sides, as shown in FIG. 4, to obtain a greater overall radiation penetration into the prosthesis 40. When the LED carrier 20 is properly placed, the LEDs 30 are powered for approximately 10 to 30 seconds to cure the prosthesis 40.

Figure 7:
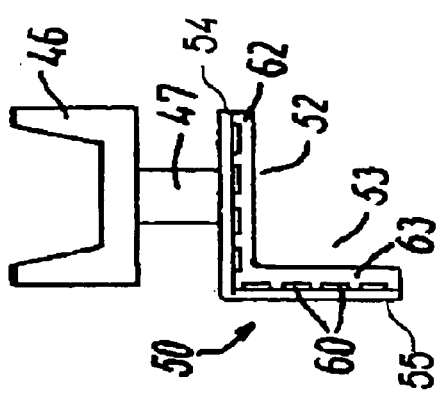
FIG. 7 is a view from another side of the curing apparatus shown in FIG. 6.
Figure 8:
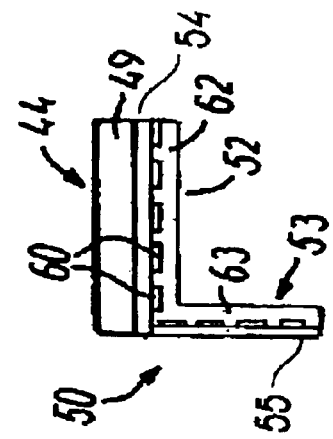
FIG. 8 shows a variation of the apparatus shown in FIGS. 6 and 7.
Figure 6:
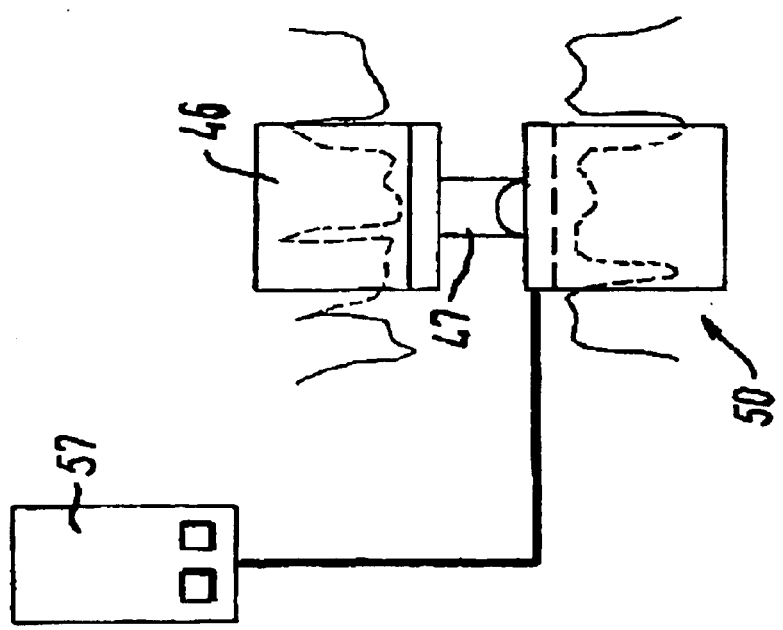
FIG. 6 is a diagrammatic side view of as second preferred embodiment of a curing apparatus.

A second preferred embodiment of the inventions is shown with reference to FIGS. 6, 7 and 8. The LED carrier 50 is in principal the same as the LED carrier 20 described above, i.e. with a longer wing 52 and a shorter wing 53, build up of circuit boards 54,55 with substantially the same surface mounted LEDs 60 under a clear coating 62,63. The LED carrier 50 is, however, not connected to any handle. Instead, at least one of the rear surfaces of the wings 52,53 is provided with a surface 44 or holder 46 to engage an opposite tooth. The holder 46 can be L- or U-shaped and may be covered with a soft resilient material. The holder 46 can be connected to the top of the LED carrier by a spacer 47.

As best shown in FIG. 8, the surface 44 for engaging the opposite tooth, may be formed by a layer 49 of soft, resilient material, such as sponge rubber of the like. The power source 57 can be of the same type described above for the first preferred embodiment. The power source 57 is connected to the LEDs 60 via a flexible cable that in use extends from the curing apparatus in the oral cavity to the power source 57 outside the oral cavity.

The LED carrier 50 is placed by an operator, usually a dentist, as shown, on a tooth containing a prosthesis 40 to be cured and the patient holds the LED carrier 50 in place between the tooth containing a prosthesis 40 to be treated and an opposite tooth. When the LED carrier 50 is properly placed, the LEDs 60 are powered for approximately 10 to 30 seconds to cure the dental material and the LED carrier 50 is removed. The procedure is repeated to build up a prosthesis 40 layer by layer.

Figure 9:
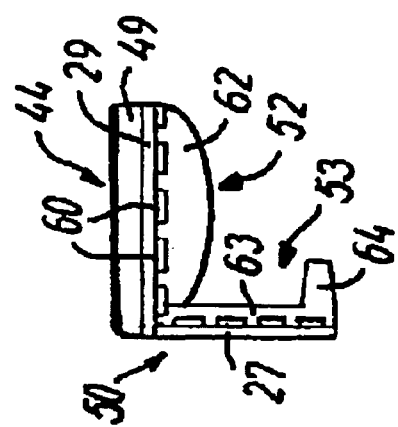
FIG. 9 shows another preferred embodiment of the curing apparatus.

FIG. 9. shows a further preferred embodiment of the curing apparatus. The LED carrier 50 is in principal the same as the lab LED carrier 20 described above, i.e. with a longer wing 52 and a shorter wing 53, build up of circuit boards 54,55 with substantially the same surface mounted LEDs 60 under a clear a covering 62,63. The clear covering may be provided in addition to the coating 32,33 shown in FIGS. 3 and 4, or in place of the coating. The clear covering is releasable from the substrate, and can be easily attached and detached from the substrate 27,29 by the dentist using the device. In one form, the clear covering is shaped in a spherical manner to create a convex lens over the LEDs 60. Thus the intensity of the radiation to the dental prosthesis 40 can be further increased. In a variation of the preferred embodiment, the clear covering is provided with a light guide 64 allowing light from the LEDs to reach a retracted dental prosthesis. Only one wing 52,53 or both wings 52,53 can be provided with a spherically shaped clear covering or with a covering having a light guide. The detachable clear coverings 62,63 can be applied to all above described preferred embodiments of the curing apparatus, with and without a handle part. The covering may also be provided in the form of a resilient pad, optically transparent, which is conformable to the tooth, or a conformable or non-conformable pad which is pre-shaped to accommodate the tooth and the restoration. Several such coverings may be provided, each with a different preformed tooth contacting surface, lens or light guide, and the dentist may select one preformed pad and attach it to the LED array as dictated by the tooth, its location, and the location and shape of the restoration.

Although the present inventions have been described in detail for purpose of illustration, it is understood that such detail is solely for that purpose, and variations can be made therein by those skilled in the art without departing from the scope of the inventions.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A light emitting apparatus for curing a photocurable dental prosthesis which has been formed in a patient's tooth, said apparatus comprising:
   a handle having an insertion portion attached thereto, said insertion portion having a distal end adapted for insertion into the mouth of the patient;
   an LED carrying part comprising a first plurality of LEDs oriented on a first plane and a second plurality of LEDs oriented on a second plane, where the first and second planes are oriented relative to each other so as to be directed to different surfaces of the tooth when the array is placed in proximity to the tooth;
   said carrying part further comprising a body with a substantially L-shaped cross-section comprising a first wing and second wing, wherein the first plurality of LED's is disposed upon the first wing and the second plurality of LED's is disposed upon the second wing;
   said first wing and second wing comprising a substrate to which the LEDs are mounted, wherein the LEDs comprise surface mounted type LEDs, and wherein said substrate comprise a printed circuit board; and
   a covering which is releasably attachable to the substrate, said covering having a convex outer surface to form a lens for focusing the radiation emitted by the LEDS.

2. A light emitting apparatus for curing a photocurable dental prosthesis which has been formed in a patient's tooth, said apparatus comprising:
   a handle having an insertion portion attached thereto, said insertion portion having a distal end adapted for insertion into the mouth of the patient;
   an LED carrying part comprising a first plurality of LEDs oriented on a first plane and a second plurality of LEDs oriented on a second plane, where the first and second planes are oriented relative to each other so as to be directed to different surfaces of the tooth when the array is placed in proximity to the tooth;
   said carrying part further comprising a body with a substantially L-shaped cross-section comprising a first wing and second wing, wherein the first plurality of LED'S is disposed upon the first wing and the second plurality of LED's is disposed upon the second wing;
   said first wing and second wing comprising a substrate to which the LEDs are mounted, wherein the LEDs comprise surface mounted type LEDs, and wherein said substrate comprise a printed circuit board; and
   a covering which is releasably attachable to the substrate, said covering comprising a light guide for focusing the radiation emitted by the LEDS.

3. A light emitting apparatus for curing a photocurable dental prosthesis which has been formed in a patient's tooth, said apparatus comprising:
   a handle having an insertion portion attached thereto, said insertion portion having a distal end adapted for insertion into the mouth of the patient;
   an LED carrying part comprising a first plurality of LEDs oriented on a first plane and a second plurality of LEDs oriented on a second plane, where the first and second planes are oriented relative to each other so as to be directed to different surfaces of the tooth when the array is placed in proximity to the tooth;
   said carrying part further comprising a body with a substantially L-shaped cross-section comprising a first wing and second wing, wherein said first wing is longer than said second wing, and wherein the first plurality of LED's is disposed upon the first wing and the second plurality of LED's is disposed upon the second wing;
   said first wing and second wing each comprising a substrate to which said LEDs are mounted, wherein the LEDs comprise surface mounted type LEDs, and wherein said substrate comprises printed circuit board;
   wherein the LEDs comprise an integral a focusing lens;
   wherein the substrate is covered with a clear coating embedding said LEDs; and
   wherein said substrate is exchangeable and locally provided with a curved outer surface to form a lens for focusing the radiation emitted by said LEDS and/or locally provided with a light guide.

4. A light emitting apparatus for curing a photocurable dental prosthesis which has been formed in a patient's tooth, said apparatus comprising:
   a handle having an insertion portion attached thereto, said insertion portion having a distal end adapted for insertion into the mouth of the patient; and
   an LED carrying part comprising a first plurality of LEDs oriented on a first plane and a second plurality of LEDs oriented on a second plane, where the first and second planes are oriented relative to each other so as to be directed to different surfaces of the tooth when the array is placed in proximity to the tooth; wherein said LED carrying part is connected to said handle by a joint having at least one degree of freedom.

5. A light emitting apparatus according to claim 4, in which said joint is a ball joint.

6. A light emitting apparatus according to claim 4, in which said joint is connected to said handle by a rod extending from a distal part of said handle to said joint.

7. A light emitting apparatus for curing a photocurable dental prosthesis in a patient's tooth, with an LED carrying body having a substantially L-shaped cross-section that comprises a first wing provided with first plurality of LEDs to be directed to a first side of said tooth, and a second wing provided with a second plurality of LEDs to be directed to a second side of said tooth, said first and second wing comprise a substrate to which said LEDs are mounted, whereby said LEDs are surface mounted type LEDS; said light emitting apparatus further comprising:

a covering which is releasably attachable to the substrate, said covering having a convex outer surface to form a lens for focusing the radiation emitted by the LEDS.

8. A light emitting apparatus for curing a photocurable dental prosthesis in a patient's tooth, with an LED carrying body having a substantially L-shaped cross-section that comprises a first wing provided with first plurality of LEDs to be directed to a first side of said tooth, and a second wing provided with a second plurality of LEDs to be directed to a second side of said tooth, said first and second wing comprise a substrate to which said LEDs are mounted, whereby said LEDs are surface mounted type LEDs; said light emitting apparatus further comprising:

a covering which is releasably attachable to the substrate, said covering comprising a light guide for focusing the radiation emitted by the LEDS.

9. A light emitting apparatus for curing a photocurable dental prosthesis in a patient's tooth, with an LED carrying body having a substantially L-shaped cross-section that comprises a first wing provided with first plurality of LEDs to be directed to a first side of said tooth, and a second wing provided with a second plurality of LEDs to be directed to a second side of said tooth, said light emitting apparatus further comprising:

an opposite tooth engaging surface, wherein said opposite tooth engaging surface is formed by a resilient layer on the back of said first or second wing.

10. A light emitting apparatus for curing a photocurable dental prosthesis in a patient's tooth, with an LED carrying body having a substantially L-shaped cross-section that comprises a first wing provided with first plurality of LEDs to be directed to a first side of said tooth, and a second wing provided with a second plurality of LEDs to be directed to a second side of said tooth, said light emitting apparatus further comprising:

an opposite tooth engaging surface, wherein said opposite tooth engaging surface comprises an L- or U-shaped member attached to the back of said first or second wing.

11. Method of curing photocurable dental prosthesis in a patient's tooth, comprising the steps of:

providing a light emitting apparatus comprising a plurality of LEDs that are mounted on a substrate, said substrate being covered with a clear coating embedding said plurality of LEDs, positioning said plurality of LEDs proximate to said photocurable dental prosthesis so that the smallest distance between the outer surface of said clear coating and the outer surface of said photocurable prostheses is less than 2 mm.

12. Method according to claim 11, in which the radiation intensity in spectral range of 440 to 500 manometer is at least 100 mw/m2.

13. Method according to claim 11, in which said light emitting apparatus is held in place by the patient between the tooth containing the prosthesis to be cured and an opposing tooth.

14. A method of curing a resinous dental restoration material after implantation of the restoration material in a tooth in a patient's mouth, said method comprising:

providing a light emitting apparatus comprising:
  a carrier having first and second section of substrate, said sections being fixed to each other at an angle suitable for accommodating the restoration material, said sections being sized and dimensioned to substantially cover a surface of the buccal, occlusal, and/or lingual surface of the tooth;
  a first array of light sources disposed on an inner surface of first section of substrate, and a second array of light sources disposed on an inner surface of the second section of substrate, said light sources being operable to illuminate the tooth with light;

placing the light emitting apparatus substantially entirely within the patient's mouth, in proximity to a tooth which has been treated with the installation of the photocurable dental restoration material;

positioning the first array of light sources in apposition to a first surface of the tooth and positioning the second array of light sources in apposition to a second surface of the tooth;

providing electrical power to first and second arrays of light sources from a power source located outside the mouth of the patient, and energizing the first and second array of light sources within the mouth of the patient.

15. The method of claim 14 further comprising the steps of:

providing a resilient biting pad on an outer surface of the first section of substrate;

placing the light emitting device in the mouth so that the first and second light arrays are in apposition to surfaces of the tooth and the biting pad is located in occluding relationship to an opposing tooth; and closing the patient's jaw to secure the light emitting device between the patient's teeth.

16. The method of claim 14 further comprising the steps of:

providing a biting cup on an outer surface of the first section of substrate, said biting cup being sized and dimensioned to accommodate an opposing tooth;

placing the light emitting device in the mouth so that the first and second light arrays are in apposition to surfaces of the tooth and the biting cup is located in occluding relationship to an opposing tooth; and closing the patient's jaw to move the occluding tooth into the biting cup and to hold the light emitting device between the patient's teeth.

17. The method of claim 14 further comprising:

providing a flexible cable extending from the light emitting device to the power source, and providing electrical power to the light emitting device through the flexible cable.

18. The method of claim 14 further comprising:

providing a rigid rod extending from the light emitting device to the power source, and providing electrical power to the light emitting device through the rigid rod;

mounting the light emitting device to the rigid rod with a ball joint;

inserting the light emitting device in the mouth and manipulating the light emitting device on the ball joint in order to orient the light emitting device to place the arrays of light sources in close proximity to the surfaces of the tooth.

* * * * *